United States Patent [19]

Cappelletti et al.

[11] Patent Number: 5,376,678
[45] Date of Patent: Dec. 27, 1994

[54] ACTIVE PRINCIPLE BASED ON AVERMECTINS, RELATED STRAIN AND PROCESS FOR THE PREPARATION THEREOF, AS WELL AS VETERINARY COMPOSITIONS CONTAINING IT

[75] Inventors: M. Leonardo Cappelletti; Giacomo Lucarelli; Giuseppe Mearelli, all of Milan, Italy

[73] Assignees: Gnosis srl; Euroresearch srl, Milan, Italy

[21] Appl. No.: 54,270

[22] Filed: Apr. 30, 1993

[30] Foreign Application Priority Data

May 5, 1992 [IT] Italy .................. MI92A1074

[51] Int. Cl.$^5$ ............... C07D 493/22; C07D 305/14; A61K 31/35; C12P 17/18
[52] U.S. Cl. ........................... 514/450; 424/115; 435/119; 435/170; 435/252.35; 435/886; 549/264; 536/7.1
[58] Field of Search ............ 435/119, 170, 252.35, 435/886; 514/28, 450; 536/7.1; 549/264; 424/115

[56] References Cited

U.S. PATENT DOCUMENTS

| | | | |
|---|---|---|---|
| 4,310,519 | 1/1982 | Albers-Schonberg et al. | |
| 4,423,211 | 12/1983 | Bagner et al. | 536/16.9 |
| 4,992,424 | 2/1991 | Banks et al. | 514/30 |
| 5,008,191 | 2/1991 | Okazaki et al. | 435/124 |
| 5,015,662 | 5/1991 | Chen | 514/450 |
| 5,120,646 | 6/1992 | Chen | 435/119 |
| 5,212,322 | 5/1993 | Okazaki et al. | 549/265 |
| 5,234,831 | 8/1993 | Hafner | 435/253.5 |
| 5,238,848 | 8/1993 | Hafner et al. | 435/253.5 |

FOREIGN PATENT DOCUMENTS

0445460A1  9/1991  European Pat. Off.

*Primary Examiner*—Herbert J. Lilling
*Attorney, Agent, or Firm*—Nixon & Vanderhye

[57] ABSTRACT

By carrying out the fermentation of *Streptomyces avermitilis* ATCC 55278, a dried mycelium is obtained which, orally administered to animals, particularly to ovines, has an antiparasitic activity.

2 Claims, No Drawings

ACTIVE PRINCIPLE BASED ON AVERMECTINS, RELATED STRAIN AND PROCESS FOR THE PREPARATION THEREOF, AS WELL AS VETERINARY COMPOSITIONS CONTAINING IT

The present invention refers to antiparasitic products for zootecnic-veterinary use and, more specifically, to an active principle based on avermectin, to the process for the production thereof, to the relevant strain, as well as to the composition for veterinary use containing it.

The avermectins form a family of eight macrolide antibiotics with 16 carbon atoms, having the following structural formula:

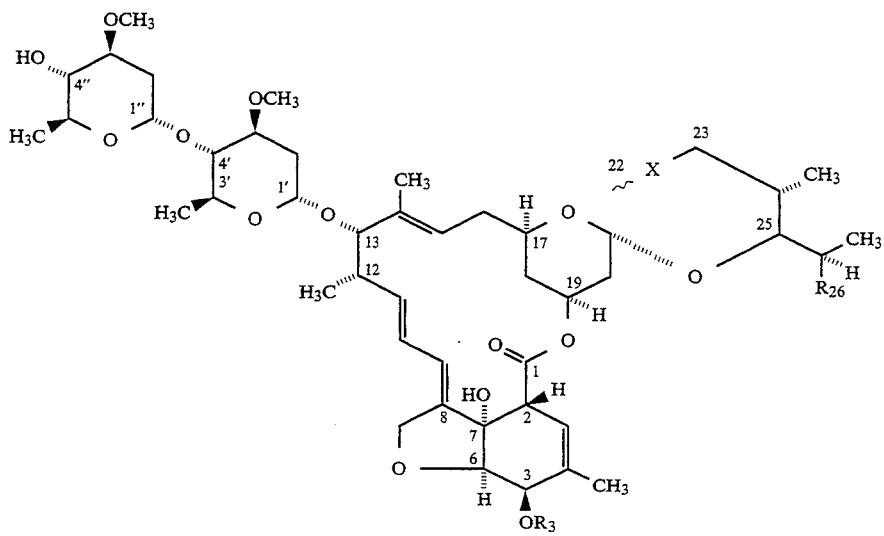

wherein:

|  | $R_5$ | $R_{26}$ | X |
|---|---|---|---|
| Avermectin $A_{1a}$ | $CH_3$ | $C_2H_5$ | $-CH=CH-$ |
| Avermectin $A_{1b}$ | $CH_3$ | $CH_3$ | $-CH=CH-$ |
| Avermectin $B_{1a}$ | H | $C_2H_5$ | $-CH=CH-$ |
| Avermectin $B_{1b}$ | H | $CH_3$ | $-CH=CH-$ |
| Avermectin $A_{2a}$ | $CH_3$ | $C_2H_5$ | $\begin{array}{c}OH\\ \mid \\ -CH_2-CH-\end{array}$ |
| Avermectin $A_{2b}$ | $CH_3$ | $CH_3$ | $\begin{array}{c}OH\\ \mid \\ -CH_2-CH-\end{array}$ |
| Avermectin $B_{2a}$ | H | $C_2H_5$ | $\begin{array}{c}OH\\ \mid \\ -CH_2-CH-\end{array}$ |
| Avermectin $B_{2b}$ | H | $CH_3$ | $\begin{array}{c}OH\\ \mid \\ -CH_2-CH-\end{array}$ |

The avermectins are obtained by fermentation starting from *Streptomyces avermitilis* (ATCC 31271) and are further obtained in purified form by the process disclosed in U.S. Pat. No. 4,310,519. However, the individual avermectins, even if separated among them, exhibit a remarkable instability, and, therefore, only an avermectin $B_1$ derivative obtained, after purification of the other seven homologues, by means of catalytic reduction of the 22–23 position bond of the aforesaid avermectin, a derivative that is named ivermectin and the chemical name of which is 22, 23-dihydroavermectin $B_1$, has found practical use.

The ivermectin is at present the main form, used in the zootecnic-veterinary field of these macrolide antibiotics and is administered for veterinary prophylaxis, exclusively in a form of an injectable speciality.

One of its uses, in a form of a gastroprotected tablet indicated for canine filariosis, is known.

Of course, the purification complexity aimed at the isolation of only the avermectin $B_1$, as well as the considerably high cost of the catalytic reduction carried out in the presence of rhodium chloride and triphenyl phosphine, and, finally, the problems involved in preparing and utilizing injectable sterile forms, make this speciality remarkably expensive.

In addition, the need of injective administration is not by itself a negligeable drawback.

On the other hand, the outstanding instability of avermectins in an acid environment excluded from the beginning their therapeutical use in forms which were not injectable or conveniently protected.

Taking also into account that the original producing microorganism, *Streptomyces avermitilis* ATCC 31271, cultivated and fermented according to the teachings of U.S. Pat. No. 4,310,519, gives rise to a very low output of avermectin, the objective limits to a wider and more general utilization of the ivermectin itself are evident. It has now surprisingly been found, and it is the main object of the present invention, that by orally administering to animals, e.g. ovines, the mycelium, obtained by fermentation, merely dried, without any purification procedure and/or separation of avermectins and/or chemical modification of them, excellent results, so far the veterinary activity is concerned, are achieved since the total disappearance of gastrointestinal strongyles and a not negligeable reduction of other parasites is observed in the treated animals.

In another embodiment of the present invention it has been found that it is possible to increase the productivity of total avermectins using a strain modified as compared with the ATCC 31271, used in the prior art, the strain, according to this invention, being the *Streptomyces avermectilis* GRL 1926 (ATCC 55278) mutant, obtained, in a way known by itself, from the above mentioned one througt a series of genetic mutation operations brought about by chemical and physical agents.

In a further embodiment, the present invention is realized with a composition having antiparasitic activity, useful in zooteenic-veterinary field and, in particular, in the treatment of ovines, suitable for oral administration, the composition being characterized in that it contains, as active principle, dried mycelium obtained as such by the fermentation of the aforesaid strain, and that the quantity of dried mycelium is such to provide a dose of at least 0.00001%, preferably between 0.00001% and 0.00008%, of total avermectins per kg of animal's live weight.

The following example illustrates the preparation of avermectins with the strain in accordance with the present invention and the obtaining of the respective mycelium. In this example, reference is made to the strain *Streptomyces avermitilis* GRL 1926 deposited on Jan. 15, 1992 with the American Type Culture Collection, located at 12301 Parklawn Drive, Rockville, Md., 20852, U.S.A., under Accession No. 55278 and therein stored accordance with the Budapest Treaty provisions.

EXAMPLE

ATCC 55278 strain is grown in 5 Erlenmeyer 250 ml flasks, containing 50 ml of culture medium A, incubated at 28° C. for two days on a table rotating at 200 rpm (2,5 cm eccentric).

At the end of this period, a 6 lts fermenter containing 4 lts of culture medium B is inoculated with the 4 flasks contents under the following operation conditions:
temperature: 22°–30° C.
stirring: 200–1200 RPM
air: 0.1–1.3 lts/lt/minute
time: 80–220 hrs At the end of this period, the culture is cooled and centrifuged to collect the mycelium, which is again suspended in 3 lts cool water and again centrifuged. The moist mycelium cake is then vacuum dried at 30°–75° C. for 16–48 hrs. At the end of the drying period, the mycelium is ground in a mill to 100–500 mesh granulometry, giving thereafter the following analytical composition data (as micrograms/gram of dry mycelium):
avermectin A1: 1.000–2.000
avermectin A2: 8.000–4.550
avermectin B1: 8.500–5.000
avermectin B2: 3.000–6.000

The total avermectins average contents 1 gram of dried mycelium is therefore 19.000 micrograms.

The compositions of the above two culture medium A and B are herebelow indicated:

| Culture medium (g/lt) | A | B |
|---|---|---|
| saccharose | 20 | 90 |
| soluble distillates | 15 | 5 |
| peanut flour | 8 | 17 |
| yeast extract | 2 | 15 |
| calcium carbonate | 15 | 3 |
| lard oil | 1 | 22 |
| Burkholder solution | 2 | 4 |
| spring water | up to 1 liter | |

With the dried mycelium of the present invention, experimental tests vivo for verifying the antiparasitic activity have been carried out:

TEST No. 1

12 sheeps weighing about 50 kg and of 7–12 months age were administered with 1 gram of dry mycelium (equal to 19 mg total avermectins) obtained as per the previous example.

After 9 and 16 days from the administration, the faeces of the treated sheeps and of 10 untreated sheeps were analyzed, so as to assess the presence of gastrointestinal strougyles (GSI), taenias and trichnuri. The presence of the SGI is measured in terms of UPG (eggs per grams of faeces).

Tables 1, 2 and 3 which follow report the tests results, wherein (−) stands for the absence and (+) for the presence of the parasite.

TABLE 1

| | PRESENCE OF PARASITES BEFORE THE ADMINISTRATION | | | |
|---|---|---|---|---|
| ANIMAL NR. | AGE (months) | SGI (EGGS PER GRAMS OF FAECES) | TRICH. | TAENIAS |
| TREATED ANIMALS | | | | |
| 1 | 7 | 300 | + | − |
| 2 | 8 | 420 | + | − |
| 3 | 8 | 380 | − | + |
| 4 | 9 | 530 | − | + |
| 5 | 7 | 550 | − | + |
| 6 | 11 | 450 | − | + |
| 7 | 9 | 280 | − | − |
| 8 | 12 | 310 | − | + |
| 9 | 12 | 750 | − | + |
| 10 | 10 | 430 | − | + |
| 11 | 8 | 370 | − | + |
| 12 | 7 | 290 | + | + |
| UNTREATED CONTROLS | | | | |
| 13 | 9 | 180 | − | + |
| 14 | 11 | 230 | − | + |
| 15 | 11 | 450 | − | + |
| 16 | 11 | 250 | + | + |
| 17 | 9 | 310 | − | + |
| 18 | 9 | 420 | − | − |
| 19 | 9 | 340 | − | + |
| 20 | 8 | 510 | − | + |
| 21 | 10 | 430 | − | + |
| 22 | 10 | 230 | − | + |

TABLE 2

| | PRESENCE OF PARASITES AFTER 9 DAYS FROM THE ADMINISTRATION | | | |
|---|---|---|---|---|
| ANIMAL NR. | AGE (months) | SGI (EGGS PER GRAMS OF FAECES) | TRICH. | TAENIAS |
| TREATED ANIMALS | | | | |
| 1 | 7 | 150 | + | − |
| 2 | 8 | 380 | + | − |
| 3 | 8 | 180 | − | + |
| 4 | 9 | 210 | − | + |
| 5 | 7 | 350 | − | + |
| 6 | 11 | 400 | − | + |
| 7 | 9 | 180 | − | − |
| 8 | 12 | 350 | − | + |
| 9 | 12 | 450 | − | + |
| 10 | 10 | 230 | − | + |
| 11 | 8 | 120 | − | + |
| 12 | 7 | 290 | + | + |
| UNTREATED CONTROLS | | | | |
| 13 | 9 | 380 | − | + |
| 14 | 11 | 430 | − | + |
| 15 | 11 | 320 | − | + |
| 16 | 11 | 510 | + | + |
| 17 | 9 | 470 | − | + |
| 18 | 9 | 520 | − | − |
| 19 | 9 | 240 | − | + |
| 20 | 8 | 440 | − | + |
| 21 | 10 | 510 | − | + |

TABLE 2-continued

PRESENCE OF PARASITES AFTER 9 DAYS FROM THE ADMINISTRATION

| ANIMAL NR. | AGE (months) | SGI (EGGS PER GRAMS OF FAECES) | TRICH. | TAENIAS |
|---|---|---|---|---|
| 22 | 10 | 290 | − | + |

TABLE 3

PRESENCE OF PARASITES AFTER 16 DAYS FROM THE ADMINISTRATION

| ANIMAL NR. | AGE (months) | SGI (EGGS PER GRAMS OF FAECES) | TRICH. | TAENIAS |
|---|---|---|---|---|
| TREATED ANIMALS | | | | |
| 1 | 7 | 0 | − | − |
| 2 | 8 | 0 | − | − |
| 3 | 8 | 0 | − | + |
| 4 | 9 | 0 | − | − |
| 5 | 7 | 0 | − | + |
| 6 | 11 | 0 | − | − |
| 7 | 9 | 0 | − | − |
| 8 | 12 | 0 | − | + |
| 9 | 12 | 0 | − | + |
| 10 | 10 | 0 | − | − |
| 11 | 8 | 0 | − | + |
| 12 | 7 | 0 | + | + |
| UNTREATED CONTROLS | | | | |
| 13 | 9 | 350 | − | + |
| 14 | 11 | 230 | − | + |
| 15 | 11 | 520 | − | + |
| 16 | 11 | 470 | + | + |
| 17 | 9 | 550 | − | + |
| 18 | 9 | 320 | − | − |
| 19 | 9 | 210 | − | + |
| 20 | 8 | 360 | − | + |
| 21 | 10 | 460 | − | + |
| 22 | 10 | 190 | − | + |

TEST No. 2

In this test the active principle dose has been halved, by orally administering 0.5 grams of dry mycelium, obtained by the procedure of the above Example, to 12 sheeps weighing about 60 kg and of 12 to 24 months age.

In this case, the faeces were analyzed after 15 and 30 days from the administration, both for the treated sheeps and for 10 control sheeps, in order to assess the adult-killing action, that is, if the antiparasitic action is extended also to the adult forms of the parasite and not only to the eggs.

The analytical results are reported in the following tables 4, 5 and 6.

TABLE 4

PRESENCE OF PARASITES BEFORE THE ADMINISTRATION

| ANIMAL NR. | AGE (months) | SGI (EGGS PER GRAMS OF FAECES) |
|---|---|---|
| TREATED ANIMALS | | |
| 1 | 13 | 250 |
| 2 | 12 | 600 |
| 3 | 15 | 1000 |
| 4 | 14 | 800 |
| 5 | 14 | 250 |
| 6 | 12 | 450 |
| 7 | 15 | 250 |
| 8 | 22 | 800 |
| 9 | 23 | 150 |
| 10 | 23 | 100 |
| 11 | 12 | 800 |
| 12 | 13 | 200 |
| 13 | 22 | 400 |
| UNTREATED CONTROLS | | |
| 13 | 12 | 200 |
| 14 | 12 | 350 |
| 15 | 12 | 300 |
| 16 | 13 | 50 |
| 17 | 12 | 550 |
| 18 | 12 | 200 |
| 19 | 23 | 40 |
| 20 | 24 | 200 |
| 21 | 23 | 10 |
| 22 | 24 | 130 |

TABLE 5

PRESENCE OF PARASITES AFTER 15 DAYS FROM THE ADMINISTRATION

| ANIMAL NR. | AGE (months) | SGI (EGGS PER GRAMS OF FAECES) |
|---|---|---|
| 1 | 13 | 0 |
| 2 | 12 | 0 |
| 3 | 15 | 0 |
| 4 | 14 | 0 |
| 5 | 14 | 0 |
| 6 | 12 | 0 |
| 7 | 15 | 0 |
| 8 | 22 | 0 |
| 9 | 23 | 0 |
| 10 | 23 | 0 |
| 11 | 12 | 0 |
| 12 | 13 | 0 |
| 13 | 22 | 0 |
| UNTREATED CONTROLS | | |
| 13 | 12 | 500 |
| 14 | 12 | 250 |
| 15 | 12 | 100 |
| 16 | 13 | 50 |
| 17 | 12 | 350 |
| 18 | 12 | 400 |
| 19 | 23 | 150 |
| 20 | 24 | 100 |
| 21 | 23 | 110 |
| 22 | 24 | 150 |

TABLE 6

PRESENCE OF PARASITES AFTER 30 DAYS FROM THE ADMINISTRATION

| ANIMAL NR. | AGE (months) | SGI (EGGS PER GRAMS OF FAECES) |
|---|---|---|
| 1 | 13 | 0 |
| 2 | 12 | 0 |
| 3 | 15 | 0 |
| 4 | 14 | 0 |
| 5 | 14 | 0 |
| 6 | 12 | 0 |
| 7 | 15 | 0 |
| 8 | 22 | 0 |
| 9 | 23 | 0 |
| 10 | 23 | 0 |
| 11 | 12 | 0 |
| 12 | 13 | 0 |
| 13 | 22 | 0 |

TABLE 6-continued

| | PRESENCE OF PARASITES AFTER 30 DAYS FROM THE ADMINISTRATION | |
|---|---|---|
| ANIMAL NR. | AGE (months) | SGI (EGGS PER GRAMS OF FAECES) |
| UNTREATED CONTROLS | | |
| 13 | 12 | 200 |
| 14 | 12 | 150 |
| 15 | 12 | 300 |
| 16 | 13 | 250 |
| 17 | 12 | 400 |
| 18 | 12 | 450 |
| 19 | 23 | 50 |
| 20 | 24 | 50 |
| 21 | 23 | 310 |
| 22 | 24 | 400 |

The test on coltivated larvae has assessed the following percentage of nematodes:
HAEMONCHUS: 39%
TRICHOSTRONGYLUS: 36%
STRONGYLOIDES: 9%
OSTERTAGIA: 10%
OESOPHAGOSTOMUM: 3%
UNIDENTIFIED: 3%

From the experimental data previously reported it clearly results the effectiveness of the dry mycelium as parasiticide, whereby the advantages of the present invention can be, in order of importance, summarized as follows:

a) the avermectins which, as already noted, are unstable in acid environment and cannot therefore withstand the action of the gastric acid environment, in the form of the present invention, i.e. bound to the mycelium as directly obtained by fermentation, reach unchanged the animal's intestine, where they are liberated, thus performing an outstanding antiparasitic activity;

b) long and expensive isolating procedures of only one avermectin from the mycelium and its subsequent catalytic conversion into ivermectin are avoided;

c) thanks to the new strain *Streptomyces avermitilis* ATCC 55278, the total yield of avermectins in the mycelium resulting from the fermentation is higher;

d) an active principle orally administerable to animals is provided for.

It is to be understood that the present invention should not be considered as limited to the ovines, but it finds similar use for other animals, in particular to breeding animals subject to the same kinds of parasites sensitive to the action of avermectins.

As regards the preparation of the composition for zootecnic-veterinary use, the usual veterinary technics are employed utilizing the customary administration vehicles.

We claim:

1. An anti-parasitic material, comprising an effective amount of a mycelium obtained by fermentation of *Streptomyces avermitilis* ATCC 55278.

2. An anti-parasitic material according to claim 1, wherein said mycelium is in dried form.

* * * * *

UNITED STATES PATENT AND TRADEMARK OFFICE
CERTIFICATE OF CORRECTION

PATENT NO. : 5,376,678
DATED : December 27, 1994
INVENTOR(S) : Cappelletti et al It is certified that error appears in the above-identified patent and that said letters patent is hereby corrected as shown below:

Column 2 line 67, delete *avermectilis*" and replace by --*avermitilis*--.

Column 3 line 1, delete "througt" and replace by --through--.

Column 4 line 6, delete "strougyles (GSI)" and replace by --stronglyes (SGI)--.

Signed and Sealed this

Fifteenth Day of August, 1995

*Attest:*

BRUCE LEHMAN

*Attesting Officer*     *Commissioner of Patents and Trademarks*